United States Patent [19]
Melder et al.

[11] Patent Number: 6,140,541
[45] Date of Patent: Oct. 31, 2000

[54] PROCESS FOR PREPARING POLYALKENE AMINES

[75] Inventors: Johann-Peter Melder, Neuhofen; Gerhard Blum, Limburgerhof; Wolfgang Günther, Mettenheim; Dietmar Posselt, Heidelberg; Knut Oppenländer, Ludwigshafen, all of Germany

[73] Assignee: BASF Aktiengesellschaft, Ludwigshafen, Germany

[21] Appl. No.: 09/180,294

[22] PCT Filed: May 20, 1997

[86] PCT No.: PCT/EP97/02571

§ 371 Date: Nov. 5, 1998

§ 102(e) Date: Nov. 5, 1998

[87] PCT Pub. No.: WO97/44366

PCT Pub. Date: Nov. 27, 1997

[30]       Foreign Application Priority Data

May 20, 1996   [DE]   Germany ............................. 196 20 262

[51] Int. Cl.$^7$ .................................................. C07C 213/00
[52] U.S. Cl. ............................................. 564/475; 564/485
[58] Field of Search ...................... 564/475, 485

[56]            References Cited

U.S. PATENT DOCUMENTS 3,756,793   9/1973   Robinson .
4,832,702   5/1989   Kummer et al. .
5,124,484   6/1992   Brown et al. ............................ 564/472
5,567,845   10/1996  Franz et al. .

FOREIGN PATENT DOCUMENTS

| | | |
|---|---|---|
| 2081853 | 5/1993 | Canada . |
| 382 405 | 8/1990 | European Pat. Off. . |
| 385 039 | 9/1990 | European Pat. Off. . |
| 476 485 | 3/1992 | European Pat. Off. . |
| 561 214 | 9/1993 | European Pat. Off. . |
| 1 405 652 | 9/1975 | United Kingdom . |
| 92/12221 | 7/1992 | WIPO . |
| 92/14806 | 9/1992 | WIPO . |

*Primary Examiner*—Samuel Barts
*Attorney, Agent, or Firm*—Keil & Weinkauf

[57]            ABSTRACT

Polyalkeneamines of the formula (I)

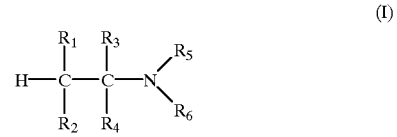

where $R_1$, $R_2$, $R_3$, $R_4$, $R_5$ and $R_6$ may have different meanings, are prepared by a process in which a polyalkene epoxide is reacted with an amine and the amino alcohol is dehydrated and reduced to give the compound of the formula (I).

12 Claims, No Drawings

PROCESS FOR PREPARING POLYALKENE AMINES

The present invention relates to a process for the preparation of polyalkeneamines from epoxides. The products prepared according to the invention are used in particular as fuel and lubricant additives.

Carburettors and intake systems of gasoline engines as well as injection systems for metering fuel in gasoline and diesel engines are increasingly being contaminated by impurities. The impurities are caused by dust particles from the air sucked in by the engine, uncombusted hydrocarbon residues from the combustion chamber and the crankcase vent gases passed into the carburettor.

These residues shift the air/fuel ratio during idling and in the lower part-load range so that the mixture becomes richer and the combustion more incomplete. Consequently, the proportion of uncombusted or partially combusted hydrocarbons in the exhaust gas and the gasoline consumption increase.

It is known that these disadvantages can be avoided by using fuel additives for keeping valves and carburettor or injection systems clean (cf. for example M. Rossenbeck in Katalysatoren, Tenside, Mineralöladditive, Editors J. Falbe and U. Hasserodt, page 223, G. Thieme Verlag, Stuttgart 1978). Depending on the mode of action and preferred place of action of such detergent additives, a distinction is now made between two generations. The first generation of additives was capable only of preventing the formation of deposits in the intake system but not of removing existing deposits. On the other hand, the additives of the second generation can prevent and eliminate deposits (keep-clean- and clean-up effect). This is permitted in particular by their excellent heat stability in zones of relatively high temperature, in particular in the intake valves.

The molecular structural principle of these additives of the second generation which act as detergents is based on the linkage of polar structures to generally higher molecular weight, nonpolar or oleophilic radicals. Typical members of the second generation of additives are products based on polyisobutene in the nonpolar moiety, in particular additives of the polyisobuteneamine type and of the polyisobutene amino alcohol type. Such detergents can be prepared starting from polyisobutenes, by various multistage synthesis processes.

Polyisobuteneamino alcohols are prepared by first epoxidizing polyisobutenes and then reacting the epoxide with the desired amine. Such processes catalyzed by homogeneous or heterogeneous catalysts are described, for example, in WO 92/12221, WO 92/14806, EP 0 476 485 and EP 0 539 821.

Polyisobuteneamines are obtained starting from polyisobutene, essentially by two processes.

The first process involves chlorination of the polymeric parent structure followed by nucleophilic substitution by amines or preferably ammonia. The disadvantage of this process is the use of chlorine, which results in the occurence of chlorine- or chloride-containing products, which is by no means desirable today and should if possible be avoided. For example, German Laid-Open Applications DE-OS 2,129, 461 and DE-OS 2,245,918 describe the reaction of halogen-containing hydrocarbons with an amine compound in the presence of a hydrogen halide acceptor.

In the second process, the polyisobuteneamines are prepared starting from polyisobutene by hydroformylation and subsequent reductive amination. For example, EP 0 244 616 and German Patent 3,611,230 describe the carbonylation of polybutene or polyisobutene in the presence of a homogeneous catalyst, eg. cobalt octacarbonyl, and the subsequent conversion of the oxo product into the amine. The disadvantages of this process are the high level of technical complexity of the carbonylation of the reactive polyisobutene under high pressure conditions and the special measures for removing the homogeneous carbonylation catalyst.

It is an object of the present invention to provide a process for the preparation of polyalkeneamines which is simpler to carry out than the processes known to date and gives an essentially halide-free product. In particular, the novel process should be capable of being carried out starting from polyalkene without the complicated oxo synthesis.

We have found that this object is achieved by providing a process for the preparation of polyalkeneamines of the formula (I)

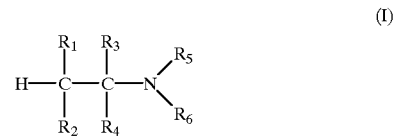

where $R_1$, $R_2$, $R_3$ and $R_4$, independently of one another, are each hydrogen or an unsubstituted or substituted, saturated or mono- or polyunsaturated aliphatic radical having a number-average molecular weight of up to about 40000, at least one of the radicals $R_1$ to $R_4$ having a number average molecular weight of from about 150 to about 40000, and $R_5$ and $R_6$, independently of one another, are each hydrogen, alkyl, cycloalkyl, hydroxyalkyl, aminoalkyl, alkenyl, alkynyl, aryl, arylalkyl, alkylaryl, hetaryl or an alkyleneimine radical of the formula (II)

where

Alk is straight-chain or branched alkylene, m is an integer from 0 to 10, and $R_7$ and $R_8$, independently of one another, are each hydrogen, alkyl, cycloalkyl, hydroxyalkyl, aminoalkyl, alkenyl, alkynyl, aryl, arylalkyl, alkylaryl or hetaryl or, together with the nitrogen atom to which they are bonded, form a heterocyclic structure, or $R_5$ and $R_6$, together with the nitrogen atom to which they are bonded, form a heterocyclic structure, it being possible for each of the radicals $R_5$, $R_6$, $R_7$ and $R_8$ to be substituted by further alkyl radicals carrying hydroxyl or amino groups, wherein an epoxide of the formula (IV)

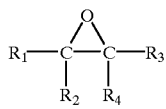

(IV)

where $R_1$, $R_2$, $R_3$ and $R_4$ have the abovementioned meanings, is reacted with a nitrogen compound of the formula (V)

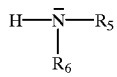

where $R_5$ and $R_6$ have the abovementioned meanings, to give the amino alcohol of the formula (VI)

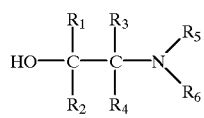

(VI)

the amino alcohol of the formula (VI) is catalytically dehydrated and the olefin formed is hydrogenated to give the amine of the formula (I).

In a first preferred embodiment, the conversion of the epoxide (IV) to the amine (I) is carried out in one stage by reacting the epoxide (IV) with the nitrogen compound (V) in the presence of hydrogen and of a catalyst which has dehydrating and at the same time hydrogenating properties.

In a second preferred embodiment, the conversion of the epoxide (IV) to the amine (I) is carried out in two stages by first reacting the epoxide (IV) with the nitrogen compound (V) in the presence of an alkoxylation catalyst to give the amino alcohol (VI) and, if necessary, separating off unconverted reactants. The amino alcohol (VI) is hydrogenated in a second stage in the presence of a catalyst which has dehydrating and at the same time hydrogenating properties to give the amine (I).

The second process variant is advantageous in particular when reactants which are capable of undergoing undesirable secondary reactions under the chosen reaction conditions are used. This may be the case, for example, when ethylenediamine is used as the nitrogen compound of the formula (V). In the presence of the catalyst used according to the invention and having dehydrating and hydrogenating properties, dimerization with formation of piperazine may take place here, it being possible to avoid this if the amino alcohol (VI) is first produced in a first process stage, unconverted amine is removed and then, after the addition of the catalyst, dehydration and hydrogenation are carried out to give the end product (I).

The catalyst which can be used according to the invention and having dehydrating and hydrogenating properties is preferably chosen from zeolites or porous oxides of Al, Si, Ti, Zr, Nb, Mg and/or Zn, acidic ion exchangers and heteropolyacids, each of which carries at least one hydrogenation metal. The hydrogenation metals used are preferably Ni, Co, Cu, Fe, Pd, Pt, Ru, Rh or combinations thereof.

Zeolites which may be used according to the invention are, for example, solid acidic zeolite catalysts which are described in EP 0 539 821, which is hereby incorporated by reference. Examples of suitable zeolites are zeolites having the mordenite, chabasite or faujasite structure, zeolites of the A, L, X and Y type, zeolites of the pentasil type having an MFI structure, zeolites in which some or all of the aluminum and/or silicon is replaced by foreign atoms, eg. aluminosilicate, borosilicate, ferrosilicate, beryllosilicate, gallosilicate, chromosilicate, arsenosilicate, antimonosilicate and bismuthosilicate zeolites or mixtures thereof and aluminogermanate, borogermanate, gallogermanate and ferrogermanate zeolites or mixtures thereof or titanium silicate zeolites, such as TS-1, ETS 4 and ETS 10.

To optimize the selectivity, conversion and lives, the zeolites used according to the invention can be doped in a suitable manner with further elements, as described, for example, in EP 0 539 821.

Doping of the zeolites with the abovementioned hydrogenation metals can be carried out in the same manner. The hydrogenation metal should be present in an amount of from 1 to 10% by weight, based on the total weight of the catalytically active material and calculated as oxide.

Further suitable catalysts having dehydrating and hydrogenating properties are oxides, preferably acidic ones, of the elements Al, Si, Zr, Nb, Mg or Zn or mixtures thereof, which are doped with at least one of the abovementioned hydrogenation metals. The oxide (calculated as $Al_2O_3$, $SiO_2$, $ZrO_2$, $Nb_2O_5$, MgO or ZnO) is present in an amount of from about 10 to 99, preferably from about 40 to 70%, by weight in the catalyst material (ie. catalytically active material). The hydrogenation metal (calculated as NiO, CoO, CuO, $Fe_2O_3$, PdO, PtO, $RuO_2$ or $Rh_2O_3$) is present in an amount of from about 1 to 90, preferably from about 30 to 60%, by weight, based on the total weight of the catalyst material. In addition, the oxides used according to the invention may contain small amounts, ie. from 0.1 to about 5% by weight (calculated for the oxides) of further elements, such as Mo or Na, in order to improve catalyst properties, such as selectivity and life.

Oxides of this type and their preparation are described, for example, in EP 0 696 572, which is hereby incorporated by reference. The preparation is preferably carried out by preparing an aqueous salt solution which contains the abovementioned catalyst components and effecting coprecipitation by adding a mineral base, eg. sodium carbonate, with or without gentle heating. The precipitate is separated off, washed, dried and calcined, for example by heating for 4 hours at 500° C.

The novel zeolites and active oxides described above can, if required, be conditioned by milling them, if necessary, to a certain particle size and molding them to give extrudates or pellets, it being possible to add mold assistants, eg. graphite.

The use of a catalyst which contains, based on the total weight of the catalytically active material, about 30% by weight of Zr, calculated as $ZrO_2$, about 50% by weight of Ni, calculated as NiO, about 18% by weight of Cu, calculated as CuO, about 1.5% by weight of Mo, calculated as $MoO_3$ and about 0.5% by weight of Na, calculated as $Na_2O$ is particularly preferred according to the invention.

Alkoxylation catalysts which are preferably added to the reaction mixture according to the invention promote the opening of the epoxide ring. Examples of suitable alkoxylation catalysts are water and alcohols, such as methanol and ethanol, mineral acids and carboxylic acids.

The polyalkene of the formula (III)

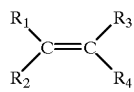
(III)

which is used as a starting material for the preparation of the epoxide of the formula (IV) is a polymer derived from at least one straight-chain or branched $C_2$–$C_{30}$-alkene, preferably $C_2$–$C_6$-alkene, in particular $C_2$–$C_4$-alkene, at least one of the radicals $R_1$ to $R_4$ having a number average molecular weight of from about 150 to 40000.

Examples of $C_2$–$C_4$-alkenes are ethylene, propylene and in particular 1-butene and isobutene.

The polyalkenes of the formula (III) which are preferably used according to the invention are reactive polyalkenes having a high proportion of terminal double bonds. A possible method for the preparation of reactive polyalkenes is described, for example, in German Laid-Open Application DE-OS 2,702,604.

Polyisobutene having a number average molecular weight of from about 800 to 1500 is particularly preferred.

Reactive polypropylenes may also be used according to the invention. These are obtained in particular by metallocene catalysis according to German Laid-Open Application DE-OS 4,205,932 and have terminal double bonds which are predominantly present as vinylidene groups. Vinyl-terminated polypropylenes are obtained, for example, according to EP 0 268 214.

The disclosure of the abovementioned patent applications is hereby incorporated by reference.

Preferred catalyst systems for the preparation of vinyl-terminated polymers are bis(pentamethylcyclopentadienyl) zirconium dichloride and bis(pentamethylcyclopentadienyl) hafnium dichloride in a solution of methylalumoxane in toluene.

Preferred catalysts for the preparation of vinylidene-terminated polymers are bis(n-butylcyclopentadienyl) zirconium dichloride, bis(octadecylcyclopentadienyl) zirconium dichloride and bis(tetrahydroindenyl)zirconium dichloride, in each case in a solution of methylalumoxane in toluene.

The polyalkenes of the formula (III) which are described above are first converted into the epoxide of the formula (IV). The epoxidation is carried out, for example, by dissolving the polyalkene in a suitable solvent, eg. diethyl ether or another dipolar aprotic solvent or nonpolar solvent, such as xylene or toluene, drying this solution if necessary, adding the epoxidizing agent and carrying out epoxidation, if required with gentle heating, for example to about 40–70° C. Conventional epoxidizing agents are used for carrying out the epoxidation. Examples of these are peracids, such as peroxybenzoic acid, m-chloroperoxybenzoic acid and peroxyacetic acid, and alkyl peroxides, such as tert-butyl hydroperoxide, m-chloroperbenzoic acid and peroxyacetic acid being preferred.

In the epoxidation, epoxides of different stereoisomeric forms may be obtained individually or as a mixture, for example compounds of the general formulae (IVa), (IVb), (IVc) and (IVd)

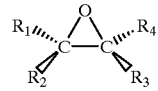
(IVa)

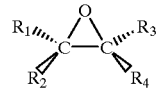
(IVb)

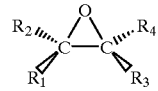
(IVc)

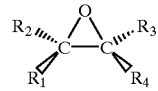
(IVd)

A certain isomer can be used for the reaction with the nitrogen compound of the formula (V); usually, however, an isomer mixture is used for carrying out the amination.

Examples of suitable nitrogen compounds of the formula (V) are ammonia, ethylene-1,2-diamine, propylene-1,2-diamine, propylene-1,3-diamine, butylenediamines and the monoalkyl, dialkyl and trialkyl derivatives of these amines, eg. N,N-dimethylpropylene-1,3-diamine. Polyalkylenepolyamines whose alkylene radicals are of not more than 6 carbon atoms, for example polyethylenepolyamines, such as diethylenetriamine, triethylenetetramine and tetraethylenepentamine, and polypropylenepolyamines may also be used. Further examples are N-amino-$C_1$–$C_6$-alkylpiperazines. Ammonia is preferably used.

In both of the process variants described above, which can be carried out either continuously or batchwise, the epoxides are reacted with the nitrogen compound of the formula (V) at from about 80 to 250° C., preferably from about 150 to 210° C., and at hydrogen pressures of up to about 600, preferably from about 80 to 300, bar. The nitrogen compound is used in a molar ratio of from about 1:1 to about 40:1, preferably in an excess of from about 5:1 to about 20:1, based on the epoxide. The reaction may be carried out either in the absence of a solvent or in the presence of a solvent (for example hydrocarbons, such as hexane, or tetrahydrofuran).

The alkyl radicals present in the compounds of the formula (I) which are prepared according to the invention include in particular straight or branched, saturated carbon chains of 1 to 10 carbon atoms. Examples are lower alkyl, ie. $C_1$–$C_6$-alkyl, such as methyl, ethyl, n-propyl, isopropyl, n-butyl, sec-butyl, isobutyl, tert-butyl, n-pentyl, sec-pentyl, isopentyl, n-hexyl and 1-, 2- and 3-methylpentyl, longer-chain alkyl, such as straight-chain heptyl, octyl, nonyl and decyl, and the branched analogs thereof.

The compounds prepared according to the invention can, if required, contain hydroxyl and aminoalkyl radicals, in which the alkyl moiety is as defined above and the hydroxyl or amino group is preferably present on a terminal carbon atom.

The alkenyl radicals present in the compounds prepared according to the invention include in particular straight or branched carbon chains having at least one carbon-carbon double bond and 2 to 10 carbon atoms. Examples of monounsaturated $C_2$–$C_{10}$-alkenyl radicals are vinyl, allyl, 1-propenyl, isopropenyl, 1-, 2- and 3-butenyl, methallyl, 1,1-dimethylallyl, 1-, 2-, 3-, 4- and 5-hexenyl, longer-chain radicals, such as straight-chain heptenyl, octenyl, nonenyl and decenyl, and the branched analogs thereof, it being possible for the double bond to occur in any desired position. According to the invention, both the cis- and the trans-isomers of the above $C_2$–$C_{10}$-alkenyl radicals are included.

The alkynyl radicals present in the compounds prepared according to the invention include in particular straight or branched carbon chains having at least one carbon-carbon triple bond and 2 to 10 carbon atoms. Examples include ethynyl, 1- and 2-propynyl, 1-, 2- and 3-butynyl and the corresponding alkynyl analogs of the abovementioned alkenyl radicals.

Examples of cycloalkyl groups which may be used according to the invention include in particular $C_3$–$C_7$-cycloalkyl radicals, such as cyclopropyl, cyclobutyl, cyclopentyl, cyclohexyl, cycloheptyl, cyclopropylmethyl, cyclopropylethyl, cyclopropylpropyl, cyclobutylmethyl, cyclobutylethyl, cyclopentylethyl and the like.

Examples of aryl radicals which may be used according to the invention are phenyl and naphthyl.

Arylalkyl radicals which may be used according to the invention are in particular phenyl-$C_1$–$C_{10}$-alkyl and naphthyl-$C_1$–$C_{10}$-alkyl, and examples of suitable alkylaryl radicals are $C_1$–$C_{10}$-alkylphenyl and $C_1$–$C_{10}$-alkylnaphthyl, the $C_1$–$C_{10}$-alkyl moiety in each case being as defined above.

The cycloalkyl, aryl and arylalkyl groups present in the compounds prepared according to the invention may contain 1 or more, eg. 1 to 4, heteroatoms, such as O, S and N, preferred heteroatoms being oxygen and nitrogen. Examples of cyclic heteroalkyl radicals are tetrahydrofuranyl, piperidinyl, piperazinyl and morpholinyl. Examples of heteroaryl groups are 5- or 6-membered aromatic ring systems which comprise from 1 to 4 of the stated heteroatoms, eg. furyl, pyrrolyl, imidazolyl, pyrazolyl, oxazolyl, isoxazolyl, oxadiazolyl, tetrazolyl, pyridyl, pyrimidinyl, pyrazinyl, pyradizinyl, triazinyl, tetrazinyl and the like. Heterocyclic groups of the same type having at least one nitrogen heteroatom may be formed from the radicals $R_5$ and $R_6$ in the above formula (I) together with the nitrogen atom to which they are bonded.

The straight-chain or branched alkylene radicals present in the compounds prepared according to the invention include straight-chain $C_1$–$C_{10}$-alkylene radicals, eg. ethylene, propylene, butylene, pentylene and hexylene, and branched $C_1$–$C_{10}$-alkylene radicals, eg. 1,1-dimethylethylene, 1,3-dimethylpropylene, 1-methyl-3-ethylpropylene, 2,3-dimethylbutylene, 1,3-dimethylbutylene, 1,1-dimethylbutylene, 1,2-dimethylpentylene and 1,3-dimethylhexylene.

Examples of substituents which are suitable according to the invention are $C_1$–$C_6$-alkyl, amino-$C_1$–$C_6$-alkyl, hydroxy-$C_1$–$C_6$-alkenyl, $C_1$–$C_6$-alkyloxy, $C_2$–$C_6$-alkenyl, $C_1$–$C_6$-alkanoyl, eg. acetyl and propionyl, nitro and amino.

The polyalkeneamines of the formula (I) which are prepared according to the invention can be used as additives for liquid or pasty lubricant compositions. At least one of the novel polyalkeneamines is contained therein, if required in combination with further conventional lubricant additives. Examples of conventional lubricant additives are corrosion inhibitors, antiabrasion additives, viscosity improvers, detergents, antioxidants, antifoams, lubricity improvers and pour point improvers. The novel compounds are usually contained in amounts of from about 1 to 15, preferably from about 0.5 to 10, in particular from 1 to 5%, by weight, based on the total weight of the composition.

Examples of such lubricants include oils and greases for motor vehicles and industrially used drive units, in particular engine oils, gear oils and turbine oils.

The compounds prepared according to the invention may furthermore be contained as an additive in fuel compositions, for example in fuels for gasoline and diesel engines. The novel compounds serve therein in particular as detergents for keeping the fuel intake system clean. Owing to their dispersing properties, they have an advantageous effect on the engine lubricant, which they may enter during operation. The polyalkeneamines prepared according to the invention are metered into commercial fuels in concentrations of from about 20 to 5000, preferably from about 50 to 1000, mg/kg of fuel. The novel additives can, if required, also be added together with other known additives.

Whereas novel additives which have a number average molecular weight of from about 2000 to 40000 are preferably used in lubricant compositions, compounds having a number average molecular weight of from about 150 to 5000, preferably from about 500 to 2500, in particular from about 800 to 1500, are particularly suitable for use as fuel additives.

Finally, compounds prepared according to the invention may also be present in combination with other additives, in particular detergents and dispersants. A combination with, for example, polyisobutylamines disclosed in U.S. Pat. No. 4,832,702 is particularly preferred.

Testing of the novel products as fuel additives, particularly with regard to their suitability as valve and carburettor cleaners, is carried out with the aid of engine tests which are performed on the test bench with a 1.2 l Opel Kadett engine according to CEC-F-04-A-87.

A spot test, as described, for example, by A. Schilling in "Les Huiles pour Moteurs et la Graissage des Moteur", Vol. 1, 1962, page 89 et seq., in slightly modified form, may be used for testing the novel products with regard to their dispersant properties.

The Examples which follow illustrate the invention.

EXAMPLES

A 50% strength solution of polyisobutene epoxide in Mihagol, which was prepared by epoxidation of Glissopal®1000 (commercial product from BASF AG), was used as a starting material in the examples below. The characterization of the aminoalkanes and of the corresponding amino alcohols was effected by determining amine numbers and hydroxyl numbers.

The catalyst used in the Examples below and having dehydrating and hydrogenating properties was prepared according to EP 0 696 572 and had the following composition (based in each case on the total weight of the catalytically active material):

30% by weight of $ZrO_2$
50% by weight of NiO
18% by weight of CuO
1.5% by weight of $MoO_3$
0.5% by weight of $Na_2O$

Example 1

One-stage, Continuous Reaction With Ammonia 125 ml/hour of a 50% strength solution of polyisobutene epoxide in Mihagol are reacted continuously with 250 ml/hour of ammonia in a 1 l tubular reactor filled with 500 g of catalyst. The reaction temperature in the reactor is from 200 to 205° C. The pressure is 250 bar and the amount of hydrogen is 100 l/hour. The readily volatile components (water, ammonia and Mihagol) are distilled off under reduced pressure (up to a bottom temperature of 70° C. at 3 mbar). The amine number of the product obtained is 30.0 and the hydroxyl number is 2.0.

Example 2

One-stage, Batchwise Reaction With Ammonia 100 g of catalyst are added to 225 g of polyisobutene epoxide, dissolved in 225 g of Mihagol and 5 g of water. In the autoclave, the mixture is heated at 200° C. for 4 hours at a hydrogen pressure of 200 bar after the addition of 450 ml of ammonia. After all low boilers have been separated off under reduced pressure, a solvent-free product having an amine number of 29.2 and a hydroxyl number of 4 is obtained, ie. the aminoalcohol was dehydrated and hydrogenated.

Example 3

Two-stage, Batchwise Reaction With Ammonia 200 g of polyisobutene epoxide are dissolved in a mixture of 200 g of Mihagol, 300 ml of tetrahydrofuran and 12 g of water. In the autoclave, the mixture is heated at 200° C. for 12 hours at a nitrogen pressure of 200 bar after the addition of 300 ml of ammonia. The readily volatile components (water, tetrahydrofuran, Mihagol) are distilled off under reduced pressure. The amine number of the product is 32.8 and the hydroxyl number is 32.2, ie. the desired amino alcohol is present.

100 g of the amino alcohol are dissolved in 400 g of Mihagol, and 100 g of catalyst are added. In the autoclave, the mixture is heated at 200° C. for 24 hours at a hydrogen pressure of 200 bar after the addition of 500 ml of ammonia. After all low boilers have been separated off under reduced pressure, a solvent-free product having an amine number of 29 and a hydroxyl number of 2 is obtained, ie. the amino alcohol was dehydrated and hydrogenated.

We claim:

1. A process for the preparation of polyalkeneamines of the formula (I)

$$\text{H}-\underset{\underset{R_2}{|}}{\overset{\overset{R_1}{|}}{C}}-\underset{\underset{R_4}{|}}{\overset{\overset{R_3}{|}}{C}}-\text{N}\underset{R_6}{\overset{R_5}{\diagup}} \quad (I)$$

where $R_1$, $R_2$, $R_3$ and $R_4$, independently of one another, are each hydrogen or an unsubstituted or substituted, saturated or mono- or polyunsaturated aliphatic radical having a number-average molecular weight of up to 40000, at least one of the radicals $R_1$ to $R_4$ having a number average molecular weight of from 150 to 40000, and $R_5$ and $R_6$, independently of one another, are each hydrogen, alkyl, cycloalkyl, hydroxyalkyl, aminoalkyl, alkenyl, alkynyl, aryl, arylalkyl, alkylaryl, hetaryl or an alkyleneimine radical of the formula (II)

$$-\!\!\!\left[\text{Alk}-\underset{\underset{R_7}{|}}{\text{N}}\right]_{\!\!m}\!\!\!-R_8 \quad (II)$$

where

Alk is straight-chain or branched alkylene, m is an integer from 0 to 10, and $R_7$ and $R_8$, independently of one another, are each hydrogen, alkyl, cycloalkyl, hydroxyalkyl, aminoalkyl, alkenyl, alkynyl, aryl, arylalkyl, alkylaryl or hetaryl or, together with the nitrogen atom to which they are bonded, form a heterocyclic structure, or $R_5$ and $R_6$, together with the nitrogen atom to which they are bonded, form a heterocyclic structure, it being possible for each of the radicals $R_5$, $R_6$, $R_7$ and $R_8$ to be substituted by further alkyl radicals carrying hydroxyl or amino groups, wherein an epoxide of the formula (IV)

$$R_1-\underset{\underset{R_2}{|}}{\overset{\overset{\displaystyle O}{\diagup\!\diagdown}}{C}}-\underset{\underset{R_4}{|}}{\overset{\overset{}{}}{C}}-R_3 \quad (IV)$$

where $R_1$, $R_2$, $R_3$ and $R_4$ have the abovementioned meanings, is reacted with a nitrogen compound of the formula (V)

$$\text{H}-\underset{\underset{R_6}{|}}{\overset{}{\text{N}}}-R_5 \quad (V)$$

where $R_5$ and $R_6$ have the abovementioned meanings, to give the amino alcohol of the formula (VI)

$$\text{HO}-\underset{\underset{R_2}{|}}{\overset{\overset{R_1}{|}}{C}}-\underset{\underset{R_4}{|}}{\overset{\overset{R_3}{|}}{C}}-\text{N}\underset{R_6}{\overset{R_5}{\diagup}} \quad (VI)$$

the amino alcohol of the formula (VI) is catalytically dehydrated and the olefin formed is hydrogenated to give the amine of the formula (I).

2. The process of claim 1, wherein the epoxide of the formula (IV) is reacted in one step with the nitrogen compound of the formula (V) in the presence of hydrogen and of a catalyst which has dehydrating and at the same time hydrogenating properties; or wherein the epoxide of the formula (IV) is first reacted with the nitrogen compound of the formula (V) in the presence of an alkoxylation catalyst to give the amino alcohol of the formula (VI) and, if required, unconverted reactants are separated off, and the amino alcohol (VI) is then hydrogenated in the presence of a catalyst which has dehydrating and at the same time hydrogenating properties.

3. The process of claim 2, wherein the catalyst having dehydrating and hydrogenating properties is selected from zeolites or porous oxides of Al, Si, Ti, Zr, Nb, Mg or Zn, acidic ion exchangers and heteropolyacids, each of which carries at least one hydrogenation metal.

4. The process of claim 3, wherein the hydrogenation metal is selected from Ni, Co, Cu, Fe, Pd, Pt, Ru, Rh and combinations thereof.

5. The process of claim 4, wherein the catalyst (catalytically active material) contains 30% by weight, calculated as $ZrO_2$, of a zirconium compound, 50% by weight, calculated as NiO, of a nickel compound and 18% by weight, calculated as CuO, of a copper compound, 1.5% by weight, calculated as $MoO_3$ of a molybdenum compound and 0.5% by weight, calculated as $Na_2O$ of a sodium compound.

6. The process of claim 1, wherein the nitrogen compound and epoxide are used in a molar ratio of from 1:1 to 40:1.

7. The process of claim 1, wherein the reaction temperature is from 80 to 250° C.

8. The process of claim 1, wherein a hydrogen pressure of up to 600 bar is established.

9. The process of claim 1, wherein an epoxide of the formula (IV), where one of the radicals $R_1$ to $R_4$ has a number average molecular weight of from 150 to 40000, is used.

10. The process of claim 9, wherein the epoxide is derived from a polyalkene which is a homo- or copolymer of $C_2$–$C_{30}$-alkenes.

11. The process of claim 10, wherein the polyalkene is derived from at least one 1-alkene, selected from ethylene, propylene, 1-butene and isobutene.

12. The process of claim 11, wherein the nitrogen compound of the formula (V) is selected from $NH_3$, monoalkylamines, dialkylamines and alkylenediamines having at least one primary or secondary amino group.

\* \* \* \* \*

UNITED STATES PATENT AND TRADEMARK OFFICE
CERTIFICATE OF CORRECTION

| | |
|---|---|
| PATENT NO. | : 6,140,541 |
| APPLICATION NO. | : 09/180294 |
| DATED | : October 31, 2000 |
| INVENTOR(S) | : Melder et al. |

It is certified that error appears in the above-identified patent and that said Letters Patent is hereby corrected as shown below:

Col. 2, line 46 and col. 10, line 1, delete the formula (II) shown and substitute:

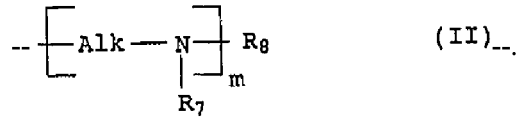

Col. 5, line 12, "$C_{2-C4}$-alkene" should be --$C_2$-$C_4$-alkene--.

Col. 12, claim 12, line 12, "claim 11" should be --claim 1--.

Signed and Sealed this

Second Day of October, 2007

JON W. DUDAS
*Director of the United States Patent and Trademark Office*